United States Patent
Wayment et al.

(10) Patent No.: US 7,063,782 B2
(45) Date of Patent: Jun. 20, 2006

(54) ELECTROCHEMICAL DETECTION OF ISCHEMIA

(75) Inventors: Hollie Wayment, Elizabeth, CO (US); Gary Fagan, Broomfield, CO (US); Peter A. Crosby, Denver, CO (US); Shannon George, Westminster, CO (US)

(73) Assignee: Ischemia Technologies, Inc., Waltham, MA (US)

( * ) Notice: Subject to any disclaimer, the term of this patent is extended or adjusted under 35 U.S.C. 154(b) by 533 days.

(21) Appl. No.: 10/304,610

(22) Filed: Nov. 26, 2002

(65) Prior Publication Data

US 2003/0132125 A1 Jul. 17, 2003

Related U.S. Application Data

(60) Provisional application No. 60/333,677, filed on Nov. 26, 2001.

(51) Int. Cl.
*G01N 27/327* (2006.01)

(52) U.S. Cl. .................. 205/792; 205/789; 205/787

(58) Field of Classification Search ... 204/400–403.01, 204/412, 416, 434; 205/789, 793, 792, 787; 600/345
See application file for complete search history.

(56) References Cited

U.S. PATENT DOCUMENTS

| | | | |
|---|---|---|---|
| 5,110,746 A | 5/1992 | Grey et al. | |
| 5,141,855 A | 8/1992 | Schmittou | |
| 5,227,307 A | 7/1993 | Bar-Or et al. | |
| 5,273,639 A * | 12/1993 | Kaneko et al. | 204/400 |
| 5,288,636 A | 2/1994 | Pollmann et al. | |
| 5,290,519 A | 3/1994 | Bar-Or et al. | |
| 5,366,609 A | 11/1994 | White et al. | |
| 5,368,707 A | 11/1994 | Henkens et al. | |
| 5,460,972 A | 10/1995 | Altura et al. | |
| 5,653,864 A | 8/1997 | Gotoh et al. | |
| 6,143,164 A | 11/2000 | Heller et al. | |
| 6,461,875 B1 | 10/2002 | Bar-Or et al. | |
| 6,475,743 B1 | 11/2002 | Bar-Or et al. | |
| 6,492,179 B1 | 12/2002 | Bar-Or et al. | |
| 6,770,487 B1 | 8/2004 | Crosby | |
| 2004/0175754 A1 | 9/2004 | Bar-Or et al. | |

FOREIGN PATENT DOCUMENTS

| | | |
|---|---|---|
| WO | PCT/US99/22905 | 10/1999 |
| WO | WO 00/20454 | 4/2000 |

(Continued)

OTHER PUBLICATIONS

Ashtamkar, S. M.; Thakkar, N. V.; "Preparation and study of an epoxy resin based cobalt (KK) ion selective electrode using a cobalt (II) complex," Jan. 2002, J. Indian Chem. Soc., vol. 79, 90-91.*

(Continued)

*Primary Examiner*—Alex Noguerola
(74) *Attorney, Agent, or Firm*—Swanson & Bratschun, LLC

(57) ABSTRACT

The subject invention comprises electrochemical methods and devices for in vitro detection of an ischemic event in a patient sample. Following addition of a known amount of a transition metal ion to the patient sample, electrodes are used to measure the current or potential difference of non-sequestered transition metal ion in the sample. The amount of non-sequestered transition metal ion in the sample reflects the degree of modification to albumin that is the result of an ischemic event.

33 Claims, 10 Drawing Sheets

FOREIGN PATENT DOCUMENTS

| WO | WO 00/78210 | 12/2000 |
| WO | WO 02/089656 | 11/2002 |
| WO | WO 02/096266 | 12/2002 |
| WO | WO 03/025571 | 3/2003 |
| WO | WO 2004/032711 | 4/2004 |
| WO | WO 04/054431 | 7/2004 |

OTHER PUBLICATIONS

Bar-Or et al. (2001) Eur. J. Biochem. 268(1):42-47.
Cai et al. (2001) J. Biochem. Biophys. Methods 47(3):209-219.
Kolthoff et al. (1977) Anal. Chem. 49(13):2108-2109.
Wang et al. (1998) Anal. Chem. 70(9):1682-1685.
Berenshtein et al. (1997) J Mol Cell Cardiol. 29(11):3025-3034.
Bradshaw et al. (1968) J Biol. Chem. 243:3817-3825.
Bradshaw et al. (1969) J. Biol. Chem. 244:5582-5589.
Christenson et al. (2001) Clin. Chem. 47:464-470.
Gryzunov et al. (2003) Arch Biochem. Biphys. 413(1):53-66.
Altura et al. (1996) Scand. J. Clin. Lab. Invest. Suppl. 224:211.
Cattrall et al. (1974) Anal. Chem. 46(14):2223.
Lakusta et al. (1979) J. Inorg. Biochem. 11:303.
Laussac et al. (1984) Biochem. 23:2832.
Masuoka et al. (1993) J. Biol. Chem. 268:21533.
Mohanakrishnan et al. (1982) J. Pharm. Sci. 71(10):1180.
Sadler et al. (1994) Eur. J. Biochem. 220:193.
Wang, Analytical Electrochemistry, 2$^{nd}$ edition, John Wiley and Sons, 2002 p. 74.
Kaku et al. (1993) Analytica Chimica Acta 272:213-220.
John et al. (1991) Analytica Chimica Acta 249:381-385.
Bar-Or et al. (2000) J. Emerg. Med. 19:311-315.
Lee et al. (1980) Am. J. Med. Technol. 46(12):853-7.
Predki et al. (1992) Biochem. J. 287:211-215.
Wang et al. (2000) Anal. Chem. 72(14):3218-22.

* cited by examiner

ELECTROCHEMICAL DETECTION OF ISCHEMIA

RELATEDNESS OF THE APPLICATION

The subject application claims the benefit of priority from U.S. Ser. No. 60/333,677, filed Nov. 26, 2001.

FIELD OF INVENTION

This invention pertains to in vitro diagnostic devices using electrochemical detection of an analyte. In particular, this invention uses redox reactions, as revealed by amperometric and potentiometric measurements in all forms (coulometry, voltammetry, ion selective electrode, chronoamperometry etc.), as an indication of an ischemic event by detecting all modifications to albumin.

BACKGROUND OF INVENTION

Ischemia is the state of imbalance of oxygen supply and demand in a part of the body often due to a constriction or an obstruction in the blood vessel supplying that part. The two most common forms of ischemia are cardiovascular and cerebrovascular.

Cardiovascular ischemia is generally a direct consequence of coronary artery disease, and is usually caused by rupture of an atherosclerotic plaque in a coronary artery, leading to formation of thrombus (blood clot), which can occlude or obstruct a coronary artery, thereby depriving the downstream heart muscle of oxygen. Prolonged ischemia can lead to cell death or necrosis, and the region of dead tissue is commonly called an infarct. Patients suffering an event of acute cardiac ischemia often present to a hospital emergency room with chest pain and other symptoms and signs, such as changes to an electrocardiogram (ECG). This type of presentation is referred to as Acute Coronary Syndrome (ACS). A patient diagnosed with ACS requires immediate treatment to avoid irreversible damage to the heart muscle.

Cerebral ischemia is often due to narrowing of the arteries leading to the brain.

Early symptoms of ischemia, which may include headache, dizziness, sensory changes, and temporary loss of certain motor function, are referred to as a Transient Ischemic Attack (TIA). TIAs are a precursor to cerebrovascular accident (CVA or stroke).

The continuum of ischemic disease includes five conditions: (1) elevated blood levels of cholesterol and other lipids; (2) build-up of atherosclerotic plaque and subsequent narrowing of the arteries; (3) reduced blood flow to a body organ (as a result of arterial narrowing or plaque rupture and subsequent thrombus formation); (4) cellular damage to an organ caused by a lack of oxygen; (5) death of organ tissue caused by sustained oxygen deprivation. Stages three through five are collectively referred to as "ischemic disease," while stages one and two are considered its precursors. It is important to distinguish between the state of ischemia and the disease that leads to it. For example, a patient with coronary artery disease is not always in the state of cardiac ischemia, but a person in the state of cardiac ischemia almost invariably suffers from coronary artery disease.

Together, cardiovascular and cerebrovascular disease accounted for 778,000 deaths in the U.S. in 1998 (2002 Heart and Stroke Statistical Update, 2002 American Heart Association). Additionally, as many as 3 to 4 million Americans suffer from what is referred to as "silent ischemia." This is a condition where ischemic heart disease is present without the usual and classic symptoms of chest pain or angina.

There is a pressing need for the development and utilization of blood tests able to predict injury to the heart muscle and coronary arteries. Successful treatment of cardiac events depends largely on detecting and reacting to the presence of cardiac ischemia in time to minimize damage. Cardiac enzymes, specifically the creatine kinase isoenzyme (CK-MB) and other markers of cardiac necrosis, specifically myoglobin and the Troponin I and Troponin T biochemical markers, are utilized for diagnosing heart muscle injury. However, these enzymes and markers are only capable of detecting the existence of cell death or necrosis, and therefore have limited or no value in patients who have ischemia without necrosis, such as those in an ischemic state prior to myocardial infarction. Additionally, these enzymes and markers do not show a measurable increase until several hours after the onset of necrosis. For instance, the cardiac troponins do not show a measurable increase above normal in a person's blood test until about four to six hours after the beginning of a heart attack and do not reach peak blood level until about 18 hours after such an event. Thus, the primary shortcoming of using markers of cardiac necrosis for diagnosis of ischemic states is that these markers are only detectable after heart tissue has been irreversibly damaged.

An array of tests are available for diagnosis of cardiac ischemia, particularly in the emergency room (see, for example, Selker, H P et al. (1997) Annals Emergency Medicine 29:13–87). The accepted standard of care is the 12 lead electrocardiogram (ECG or EKG) that, nevertheless, has a clinical sensitivity of less than 50% (see for example, Selker, H P et al. (1997) Annals Emergency Medicine 29:13–87 and Selker, H P et al. Emergency Diagnostic Tests for Cardiac Ischemia, Blackwell Science ISBN 0-632-04304-0 (1997)). Other diagnostic tests include echocardiography, and radionuclide myocardial perfusion imaging.

Diagnosis of coronary artery disease is done either by imaging (e.g., coronary angiography) or by provocative testing, where the intent is to deliberately induce cardiac ischemia and observe the effects. For example, in the ECG exercise stress test, the patient is exercised at an increasing rate to see if symptoms of ischemia are evoked, or if changes indicative of ischemia can be observed on the ECG. Stress ECG is commonly used as an initial screen for coronary artery disease, but is limited by its accuracy rates of only 25–50% (see for example, Froelicher, V F et al. (1988) Ann. Intern. Med. 128(12):965–974). Another commonly used diagnostic test is myocardial perfusion imaging, in which a radioactively tagged chemical is injected during stress testing. Normally metabolizing cardiac tissue is able to take up the radioactively tagged chemical, and is visualized using conventional imaging techniques (PET or SPECT scanning) thereby allowing differentiation between viable and damaged cardiac tissue.

The present invention, however, is believed to be advantageous over the known methods of diagnosis in that it is a simple blood test which will offer comparable accuracy at far lower costs and decreased risk and inconvenience to the patient. It is believed that the present invention provides specificity and sensitivity levels that are comparable in accuracy to current diagnostic standards.

Although there are well established biochemical markers of myocardial necrosis which can be detected in a blood sample using a point of care (POC) instrument, other than as described below in relation to the ACB™ Test, there are no well established biochemical markers for ischemia, and presently no POC instrument for detection of ischemia. An ideal test would be a blood test, preferably administered with a small, simple device providing quick, accurate results that can be used to test for disease, for example at the bedside of a patient with minimal amount of discomfort.

One component of blood is human serum albumin (HSA). Exposure of HSA to ischemic tissue produces modifications to the N-terminus (Bar-Or, D. et al. (2000) J. Emerg. Med. 19:311–315; PCT/US99/22905), and possibly other sites, on the albumin molecule. The N-terminus of albumin has been well characterized as being the primary binding site for several transition metals such as cobalt, nickel and copper (Sadler, P. et al. (1994) Eur. J. Biochem. 220:193–200; Lakusta, H. et al. (1979) J. Inorg. Biochem. 11:303–315; Gasmi, G. et al. (1997) J. Peptide Res. 49:500–509; Predki, P. et al. (1992) Biochem. J. 287:211–215; Lussac, J. et al. (1984) Biochem. 23:2832–38; Matsuoka, J. et al. (1993) J. Biol. Chem. 268:21533–37). Once the N-terminus and possibly other sequestering binding sites have been modified by exposure to ischemic tissue, they are rendered unable to bind metals. This altered albumin is referred to herein as Ischemia Modified Albumin (IMA). Therefore, if a known amount of a transition metal is added to a biological sample (patient sample comprised of whole blood, serum or plasma, urine, cerebrospinal fluid, saliva and the like), normal albumin and IMA can be differentiated by monitoring the amount of non-binding metal. Metal added to the sample will be sequestered at the N-terminus and possibly other sites on albumin more frequently in a non-ischemic sample than in an ischemic sample in which albumin has been modified in such a way that it can no longer bind the metal. The metal not sequestered at the N-terminus and possibly other sites on albumin in the samples can then be detected and quantified using the Albumin Cobalt Binding (ACB) Test (Ischemia Technologies, Inc., Denver, Colo.), which, as described in PCT/US99/22905, filed Oct. 1, 1999, and U.S. Pat. No. 5,227,307, uses calorimetric methods to determine the amount of IMA present in the sample. PCT/US99/22905 also provides a detailed description of the N-terminal modifications to albumin during an ischemic event. Studies have been conducted demonstrating the clinical utility of IMA via the ACB test in diagnosing and risk stratifying patients.

The ACB Test uses a laboratory chemistry analyzer to quantify IMA, but presently, there are no POC tests for ischemia. An ideal test would be a blood test, preferably administered with a small, simple device providing quick, accurate results referenced to a standard curve with a quality control system that can be used to test for disease at the bedside of a patient with minimal amount of discomfort. The aim of this invention is to provide such a diagnostic test.

It is an object of the subject invention to provide a diagnostic test that detects a change in a biological molecule by detecting a signal produced or altered by the change in the biological molecule, wherein the change relates to the binding of a metal to a portion of the biological molecule.

Another object is to provide a diagnostic test that determines a difference in current or potential measurements in biological fluids from ischemic patients and non-ischemic individuals, wherein the samples are first combined with cobalt or another transition metal.

It is another object of the subject invention to provide an electrochemical assay for detecting a biological condition via detection of metal binding with a biological sample, wherein there is a difference in signal relative to the amount of additives such as metal, complexing reagent or other reagents added to the biological sample where the signal is standardized using a calibration and quality control system.

Another object of the subject invention is to use data processing techniques to identify features of the electrochemical output data from an electrochemical assay for determining the differences between ischemic and non-ischemic individuals.

It is a further object of the subject invention to provide an apparatus for assaying a patient's condition at the patient's bedside.

SUMMARY OF THE INVENTION

The subject invention concerns the electrochemical detection of non-sequestered transition metal ion in a biological sample to which a known amount of transition metal has been added. The amount of non-sequestered metal ion reflects the degree of ischemia modified albumin, which in turn can be used to determine the occurrence or nonoccurrence of an ischemic event.

In one embodiment, the subject invention concerns a method for in vitro detection or measurement of albumin derivatives, which can be diagnostic of an ischemic event. This method comprises the steps of: providing a patient sample comprising albumin and/or derivatives thereof in a vessel that is connected to an electrochemistry apparatus; operating the electrochemistry apparatus to utilize an electrochemical technique; optionally offsetting a background characteristic electrochemical output signal of the sample; adding a known (optionally excess) amount of a transition metal to the sample, whereby at least some of the ion binds to said albumin metal sequestering sites and remaining ion is non-sequestered; optionally adding an indicator or amplifier to the sample to bind to the non-sequestered ion; measuring the characteristic electrochemical output signal associated with the non-sequestered ion; optionally using a standard curve to convert the output signal into a value; whereby the measured or the converted value, if it exceeds a predetermined value, can be diagnostic of an ischemic event. In this embodiment, the characteristic electrochemical output signal may be current or voltage.

In another embodiment, the subject invention comprises a method for in vitro detection or measurement of albumin derivatives, which can be diagnostic for an ischemic event comprising: providing a patient sample comprising albumin and/or derivatives or modifications thereof in a vessel having a reference electrode, a working electrode and an optional auxiliary electrode, said electrodes being connected to a potentiostat; operating the potentiostat to apply a potential to the sample; optionally offsetting a background current from redox reactions in the sample to zero; adding a known (optionally excess) amount of a transition metal ion to the sample, whereby at least some of the ion binds to said albumin N-terminus and possibly other sequestering sites and the remaining ion is non-sequestered; optionally providing an indicator or amplifier to the sample to bind to the non-sequestered metal ion; permitting the reaction of ion and albumin to reach equilibrium or a predetermined processing time; and measuring the current associated with the non-sequestered ion. The measured current can then be referenced to a standard curve and converted to a value. The measured current, or the converted value, is related to the concentration of the non-sequestered metal ion, and is therefore related to the amount of IMA. Thus, a predetermined value can be established, below which the sample can be said to be non-ischemic, and above which the sample can be said to be ischemic.

In measuring the non-sequestered metal ion, it is possible to measure not only free metal, i.e., metal not bound to albumin, but also metal ion that is bound to albumin, but in such a manner as to remain non-sequestered from detection. As used herein, "non-sequestered" ions refer not only to free ion that is not bound to albumin, but also to ions that are loosely associated with albumin but which remain non-sequestered. Non-sequestered metal ions may be measured directly by electrochemical techniques or using an indicator or amplifier complexes such as dimethylglyoxime (DMG), dithiothreitol (DTT) or common covalent chelating agents such as EDTA and the like, according to methods known in the art. Indicators or amplifiers may be incorporated into the electrode amalgam, or may be added to the sample vessel before, during or after addition of the metal ion. Indicators and amplifiers may also be attached to a solid-phase in such a manner as to remain capable of binding metal ions, thereby allowing for phase separation of the indicator/amplifier signal from the reaction mixture. The indicators/amplifiers bind to the non-sequestered metal ion and permit the measurement of the metal ion in the current embodiment of the subject invention. While the detection of current associated with non-sequestered metal ions may be enhanced by the use of indicators or amplifiers, it may also be possible to detect the current associated with non-sequestered metal ions without indicators or amplifiers.

In another embodiment, the subject invention comprises a method for in vitro detection or measurement of albumin derivatives which may be diagnostic for an ischemic event comprising: providing a patient sample comprising albumin and/or derivatives or modifications thereof in a vessel having an ion selective electrode and a reference electrode, wherein the two electrodes are connected to an electrostat or a voltmeter, and wherein the ion selective electrode comprises a barrier that is selectively permeable to a transition metal ion; operating the electrostat/voltmeter to measure the potential difference between the reference electrode and the ion selective electrode in contact with the sample; optionally offsetting the background potential difference of the sample; adding a known (optionally excess) amount of the transition metal ion to the sample, whereby at least some of the ion binds to the N-terminus and possibly other sequestering sites of the albumin and the remaining ion is non-sequestered; optionally providing an indicator or amplifier to the sample to bind with the non-sequestered metal ion; permitting the non-sequestered metal ion to cross the membrane of the ion selective electrode; and measuring the voltage associated with the ion activity difference across the ion selective electrode's barrier. This voltage change can be related to a standard calibration curve and converted to a value. The measured voltage, or the converted value, is related to the concentration of the non-sequestered metal ion, and is therefore related to the amount of IMA. Thus, a predetermined value can be established, below which the sample can be said to be non-ischemic, and above which the sample can be said to be ischemic.

The subject invention also comprises a device for in vitro electrochemical detection or measurement of albumin derivatives which can be diagnostic for an ischemic event comprising: an electronics module housing having a display means, a data entry and control means, an aperture, internal contacts in said aperture for electrical continuity with the display means, a power source, and optionally a link to a laboratory information system; and a sample analysis strip comprising a sample well, and a plurality of electrodes, wherein each electrode is positioned in the sample well and connected via a corresponding trace to a corresponding contact on the strip; wherein insertion of the strip into the module housing engages each strip contact with its corresponding module contact, which permits electrical continuity with the display means, whereby the albumin derivatives may be detected and/or measured. The link to a laboratory information system is possible via several means, including a direct electrical connection, an infrared link or a wireless link. This device can be used with either the current or the potential difference embodiments for detection of an ischemic event in a biological sample.

In a further embodiment, the invention provides a device for in vitro electrochemical detection or measurement of albumin derivatives in a sample which may be diagnostic for an ischemic event. This device comprises: a housing having an aperture for receiving a sample analysis strip, the sample analysis strip having a sample well, a plurality of electrodes positioned in the sample well and a like plurality of first contacts interconnected to the electrodes; control means within the housing; and a plurality of second contacts in the aperture electrically coupled with the control means for interconnecting with the plurality of first contacts when the sample analysis strip is inserted within the aperture. Upon insertion of the sample analysis strip into the aperture, each first contact engages a corresponding second contact whereby the albumin derivatives can be detected or measured by said control means. This device can include a link to a laboratory information system., which may be a direct electrical connection, an infrared link or a wireless link. The device may also have display means within the housing which is electrically coupled with the control means; the display means displays information indicative of detected albumin derivatives. The device may also have data entry means electrically coupled to the control means. The control means includes means for measuring a characteristic electrochemical output signal associated with the sample in the sample analysis strip; and means for determining whether the electrochemical output signal exceeds a predetermined value, whereby an ischemic event is indicated. The electrochemical output signal can be a current associated with non-sequestered metal ion in the sample to which has been added a known amount of a transition metal ion. Alternatively, the electrochemical output signal can be a potential difference measured by an ion selective electrode which has a barrier that is selectively permeable to a transition metal ion, where the potential difference is measured in sample to which a known amount of a transition metal ion has been added.

All references cited herein are incorporated in their entirety by reference.

DETAILED DESCRIPTION OF THE INVENTION

Figure 1:
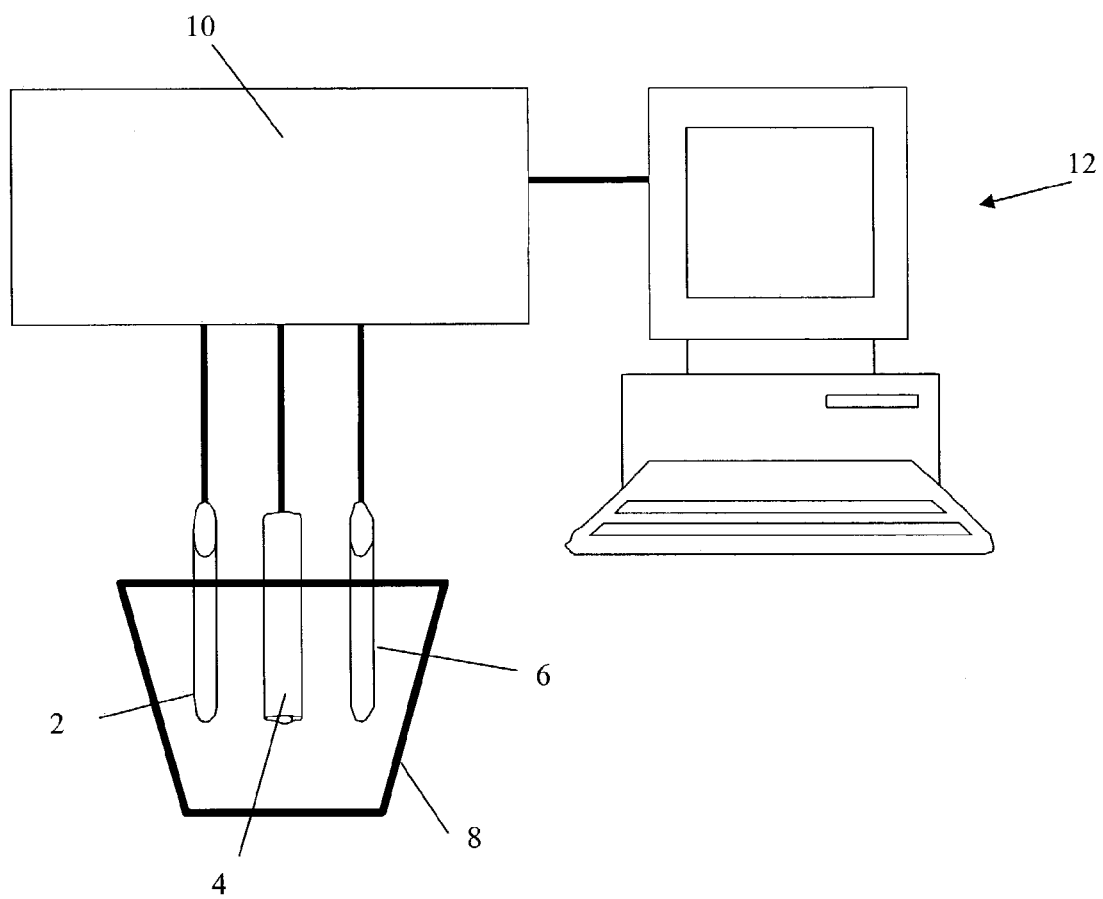
FIG. 1 illustrates the components required for an electrochemical measuring device.

The following definitions are provided to assist in the understanding of the subject invention.

"IMA" refers to ischemia induced modifications to albumin that affect the transition metal binding capacity of the molecule. IMA includes albumin N-terminal derivatives, albumin with derivatized non N-terminal metal binding sites, which when non-derivatized, are capable of sequestering metals from detection, and full length albumin that has a copper occupied N-terminus.

"Albumin N-terminal derivatives" refers to those species of albumin that are altered or truncated at the N-terminus as a result of an ischemic event. Specifically, the derivatives include those albumin species lacking 4, 3, 2 and 1 N-terminal amino acids, as well as a full-length albumin that is acetylated or otherwise derivatized at its terminal Asp residue. Albumin-terminal derivatives cannot form albumin-metal complexes and may be found in the blood of ischemic patients.

"Excess amount" of metal ion or "excess metal ion" refers to addition of an amount of metal ion that will substantially exceed the stoichiometrically available albumin metal ion binding sites such that substantially all full-length albumin is bound to metal ion at its N-terminus and substantially all albumin is bound to metal ion at other metal binding/sequestering sites, if any.

An "indicator", "amplifier" or "complexing agent" is a compound that forms a complex with the transition metal that is non-specifically bound to the albumin, e.g., at non-N-terminus functional sites including thiol groups. Examples of indicators or amplifiers are DMG, DTT and common divalent chelating agents such as ethylenediaminetetraacetic acid (EDTA) and the like. These compounds permit or enhance the measurement of the contribution of the non-sequestered metal ions that are loosely associated with albumin, to the current or voltage in the subject embodiments. See, e.g., Lee et al. (1980) Am. J. Med. Technol. 46(12):853–7; and Wang et al. (2000) Anal. Chem. 72(14):3218–22.

"Non-sequestered" ions, as discussed above, means free ions that are not bound to albumin, and ions that are loosely associated with albumin but which remain non-sequestered, i.e., capable of measurement by direct or indirect electrochemical techniques. Indirect electrochemical techniques involve the use of complexing agents.

"Patient sample" means any patient sample that contains albumin (full length and/or derivatives), and can include whole blood, serum, plasma, other blood fraction, urine, saliva, cerebrospinal fluid, breast milk or the like. "Predetermined processing time" refers to a selected time after addition of the transition metal at which measurements are consistently taken. The predetermined processing time may be shorter than the time required for the achievement of equilibrium.

"Predetermined value" refers to that current value, potential difference value, a value derived from a standard curve or the like that has been determined by clinical tests with normal individuals and ischemic patients to be the cutoff value above which an ischemic event is indicated.

"Sequestered" ions are metal ions that are coordinated (bound) to albumin in such a manner as to be rendered incapable of reacting with a complexing agent or in such a manner as to prevent the complexing agent from stripping the bound metal from albumin.

"Transition metal" refers to any transition metal of the Periodic Table. A preferred transition metal is cobalt.

According to the subject invention, albumin modified at the N-terminus and possibly other metal sequestering sites, can be differentiated from non-modified albumin by monitoring the current resulting from redox reactions of transition metals, or potentiometrically as with an ion selective electrode. Both systems require only that the metal analyte bound at the N-terminus and possibly other metal sequestering sites of albumin not be detectable electrochemically.

A current measurement resulting from a redox reaction can be made by applying a potential specific to the analyte of interest to the system. In a more specific case, a known concentration of a metal is introduced to the sample. As the metal is sequestered at the N-terminus or elsewhere, it is no longer available to participate in an electrochemically detectable reaction and therefore can no longer be detected. The time interval for current stabilization will be dependent on the binding kinetics of the metal to the metal sequestering sites on albumin. IMA cannot sequester metals to the same degree as non-IMA albumin, therefore the resulting current in a sample with a relatively large amount of modified albumin (an ischemic sample) will be different than a sample with very little modified albumin (a normal sample). The type of reaction taking place will determine the type of current flow. For example, if an oxidizing potential is applied, the analyte present in the reaction is being forced from $M^+ \rightarrow M^{2+} + e^-$, rendering electron(s) free for current flow. The converse is true for a reducing potential is applied as the reaction is now being forced from $M^+ + e^- \rightarrow M(s)$, where the system must provide electrons. Therefore, the increased free metal results in a negative current flow within the system. The working electrode measures a net current flow regardless of the direction in which current flows. This system is sensitive enough such that only small variations in the analyte will result in significant changes in net current flow. An amplification system as described herein may or may not be incorporated into the system to increase sensitivity.

Potential difference measurements can also be used to measure the amount of IMA in a sample. Measurements can be made by placing both the reference electrode and the ion selective electrode (specific for the analyte being measured) or a combination electrode (also specific to the analyte being measured) into the sample. A potential measurement of the sample is made based on the amount of analyte that can be measured by the ion selective electrode and the reference electrode. The analyte in the proper ratio with albumin can then be added. The potential difference between the ion selective electrode and the reference electrode will change depending on the amount of analyte left after the analyte is sequestered by albumin and when sufficient migration of the analyte to the ion selective electrode has taken place.

Current Detection Methods

Although there are a variety of techniques for electrochemical detection of an analyte, in the current embodiment, the electrochemical system measures current changes. A general electrochemical system, as shown in FIG. 1, requires two or three electrodes, a working electrode 2, reference electrode 4 and optional auxiliary electrode 6, in contact with each other via a solution in a vessel 8. The electrodes are connected to a potentiostat 10 that applies a potential and measures a current which is transferred as a signal to an appropriate output device such as a computer 12 or strip chart recorder.

Figure 2:
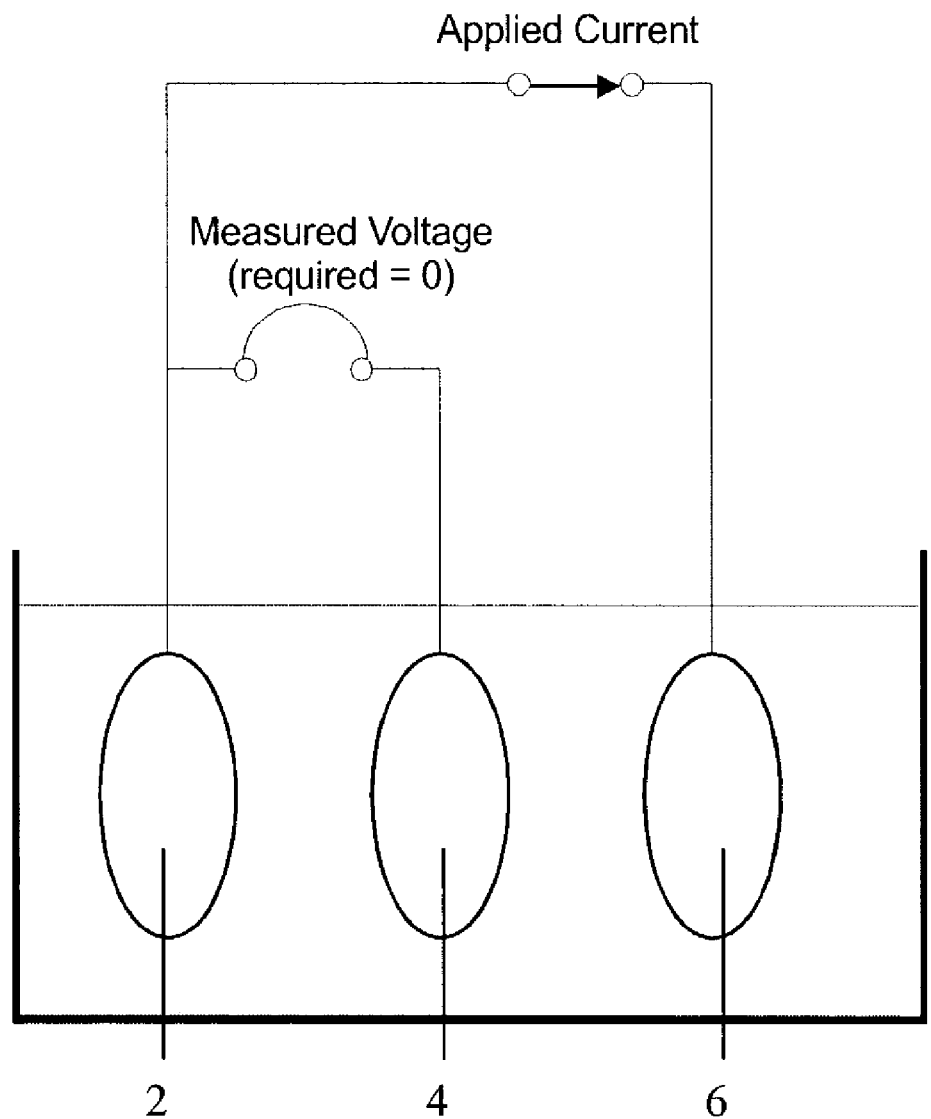
FIG. 2 illustrates the basic components of a functioning potentiostat.

Conceptually, a potentiostat consists of two electrodes in a solution, one of which is the reference electrode against which all voltage measurements are referenced. However, in general, reference electrodes only act properly as a reference when there is no current passing through them. Therefore, depending on the amount of current being produced it may be necessary to have an additional electrode, an auxiliary electrode, through which current can pass, but which is kept at the same voltage as the reference electrode. The basic components of a functioning potentiostat are shown in FIG. 2. Three electrodes, the reference 4, working 2, and auxiliary 6 electrodes, are placed in a solution containing the ionic species to be measured. A current is passed between the auxiliary electrode 6 and the working electrode 2. As the current is changed (increased or decreased, or change in polarity), the voltage between the working electrode 2 and the reference electrode 4 is measured, and the current adjusted until the voltage is zero. At this point, the voltage at the working electrode 2 is exactly the same as the voltage at the reference electrode 4, but no current is passing through the reference electrode 4. The precise details of a working potentiostat are well known to those skilled in the art.

Redox reactions involve the transfer of electron(s). An oxidized species is one that has given up electron(s) to another species. The species that accepts the electron(s) is then said to be a reduced species. The direction in which these electrons flow is driven by a standard redox potential (designated by $E°$). Redox half reactions for cobalt are:

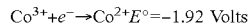

$$Co^{3+}+e^- \to Co^{2+} \quad E°=-1.92 \text{ Volts}$$

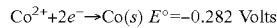

$$Co^{2+}+2e^- \to Co(s) \quad E°=-0.282 \text{ Volts}$$

$E°$ are set relative to a standard hydrogen reference electrode (at standard temperature, pH and activity), and therefore must be adjusted based on the type of reference electrode being used. For example, a Ag/AgCl reference electrode requires a shift in $E°$ by 0.197 Volts. So $Co^{3+}+e^- \to Co^{2+}$ would now require $-2.117$ Volts to drive the reaction. Potentials more positive than $E°$ will force the species to be in the oxidized form while potentials less than $E°$ will force the species into the reduced form. This is in compliance with the Nernst equation for a half reaction, which states:

$$E=E°-(RT/nF)\ln([Red]/[Ox])$$

Where
  $E$=Applied potential
  $E°$=Standard redox potential of the reaction (adjusted for the type of reference electrode being used)
  $R$=a constant of 8.314 J/K·mol
  $T$=Temperature in K
  $n$=number of electrons transferred in the reaction
  $F$=Faraday's constant ($9.648 \times 10^4$ C/mol)
  $[Red]$=the concentration of the reduced species
  $[Ox]$=the concentration of the oxidized species As electrons are passed from one species to another they can be detected as current and quantified.

Redox reactions can be measured in complex matrices, i.e., mixtures or solutions of many materials. Systems for measurement of these reactions require that a potential can be applied to the system relative to a reference electrode. The system requires a potentiostat capable of applying the appropriate potential, measuring the current within working range, and an offset capable of removing background current; a working electrode; a reference electrode and possibly the use of an auxiliary electrode.

The working electrode is the site at which the reaction of interest (i.e. the transfer of electrons) occurs. The working electrode can be any solid-state electrode including, but not limited to, platinum, carbon, graphite, gold and mercury/metal amalgam. These solid-state electrodes may or may not be required to be separated from matrix proteins to prevent protein build up on the electrode surface. Polymer coatings or some other filter or barrier separation may be used. Polymer coatings may include, but are not limited to, perfluorosulfonate (Nafion™) and cellulose acetate. The working electrode may also be a semi-solid state or liquid electrode including, but not limited to, carbon paste, mercury film and mercury drop electrodes.

The reference electrode provides a relative point for the working electrode to maintain the desired potential. Reference electrodes can be made from silver wire, silver/silver chloride, platinum, carbon, graphite, gold as well as any other solid-state, semi-solid state, and liquid electrode.

The auxiliary electrode acts to maintain a zero current (preventing current build up) between the reference electrode and the working electrode such that the only current being measured is resulting from the analyte. Auxiliary electrodes may be any of the solid-state electrodes indicated above.

Figure 3:
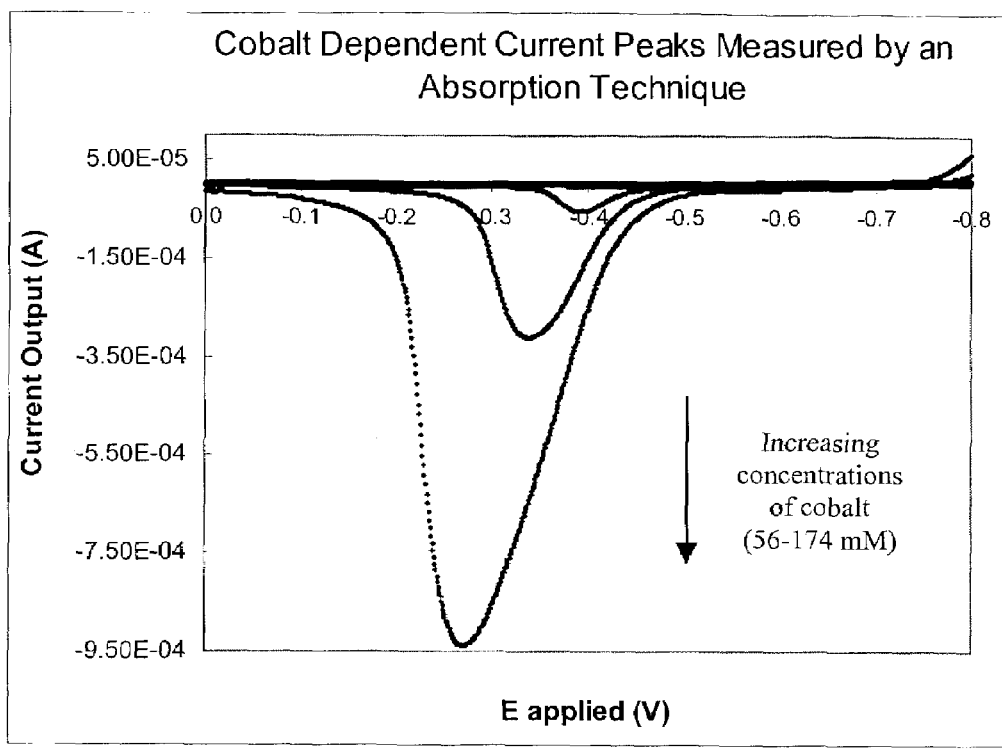
FIG. 3 shows a graph of cobalt dependent current peaks measured by an adsorption technique.

Working electrodes may be used as a substrate onto which a species is adsorbed via a redox reaction and then removed and measured with a second redox reaction (see Joseph Wang, Analytical Electrochemistry, $2^{nd}$ edition, John Wiley and Sons, 2002). Such techniques are commonly referred to as adsorption or stripping voltammetry. Example 1 describes and FIG. 3 shows the results of such a technique. It was found that increasing concentrations of cobalt added to the sample resulted in corresponding increases in measured current, demonstrating that the current being generated is in fact cobalt dependent.

Figure 4:
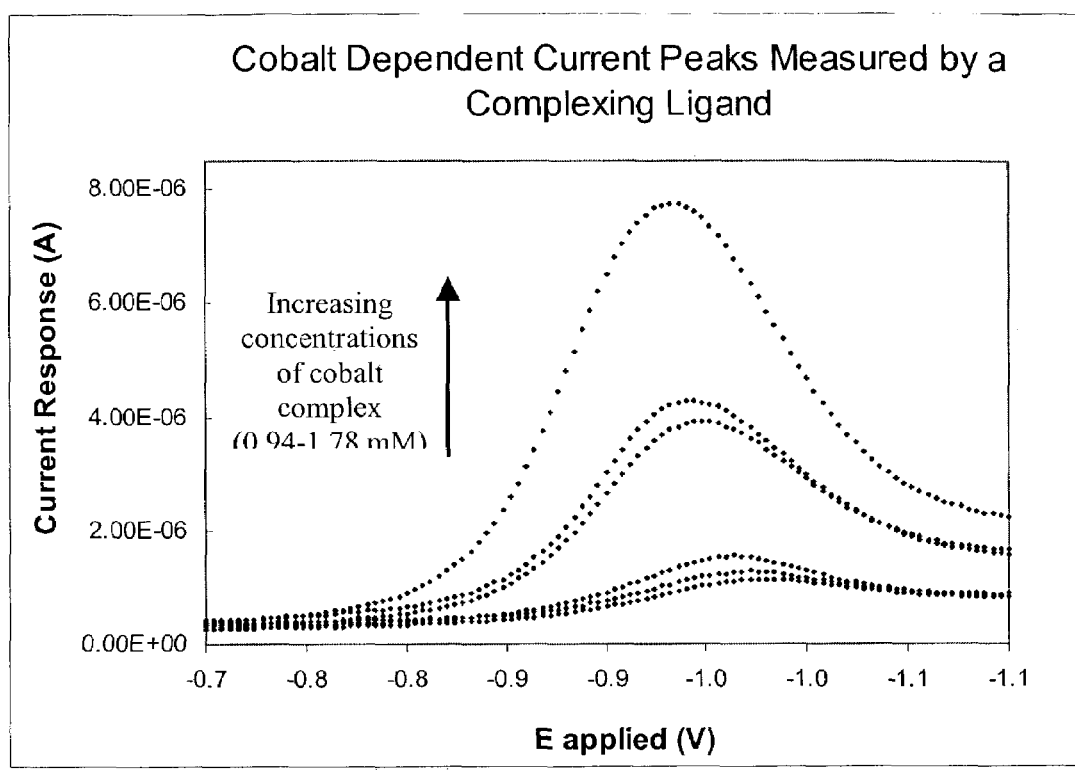
FIG. 4 shows a graph of the cobalt dependent current peaks measured by a complexing ligand using a voltammetry technique.

Complexing agents (i.e., indicators or amplifiers) may be added to systems to enhance the signal response of a non-sequestered analyte. Example 2 describes and FIG. 4 illustrates that addition of an excess amount of complexing agent to samples containing increasing concentrations of cobalt ion can enhance the measured current associated with the non-sequestered metal ion. The complexing agent forms a complex with the metal ion, and this complex is measurable in the form of current. Control experiments in which only Co ion or complexing agent was added did not produce a current at the same potentials. The current-generating potential applied to detect the complex of metal ion and complexing agent is typically different from the current-generating potential applied to detect free metal ion in the sample.

Using the complexing agent technique to detect non-sequestered cobalt ion, it has been found that individuals that test positive for ischemia using the ACB™ Test had non-sequestered cobalt complex concentrations as indicated by measured current that showed a significant separation from measured current for non-ischemic samples.

Figure 5:
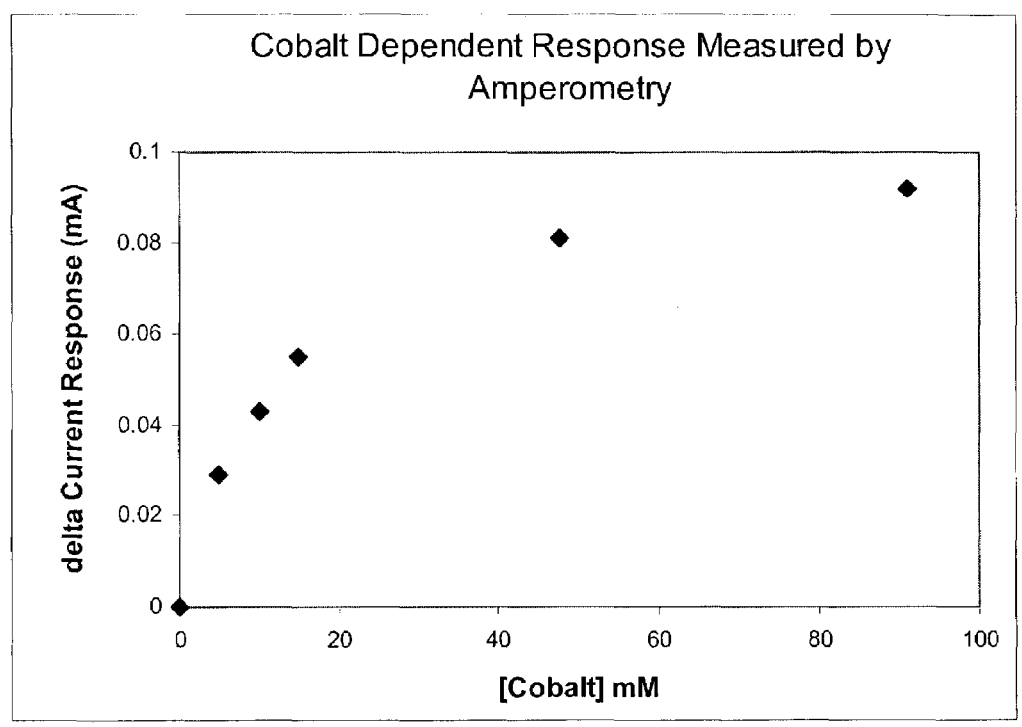
FIG. 5 shows a data output profile of a cobalt current response measured by amperometry.
Figure 6:
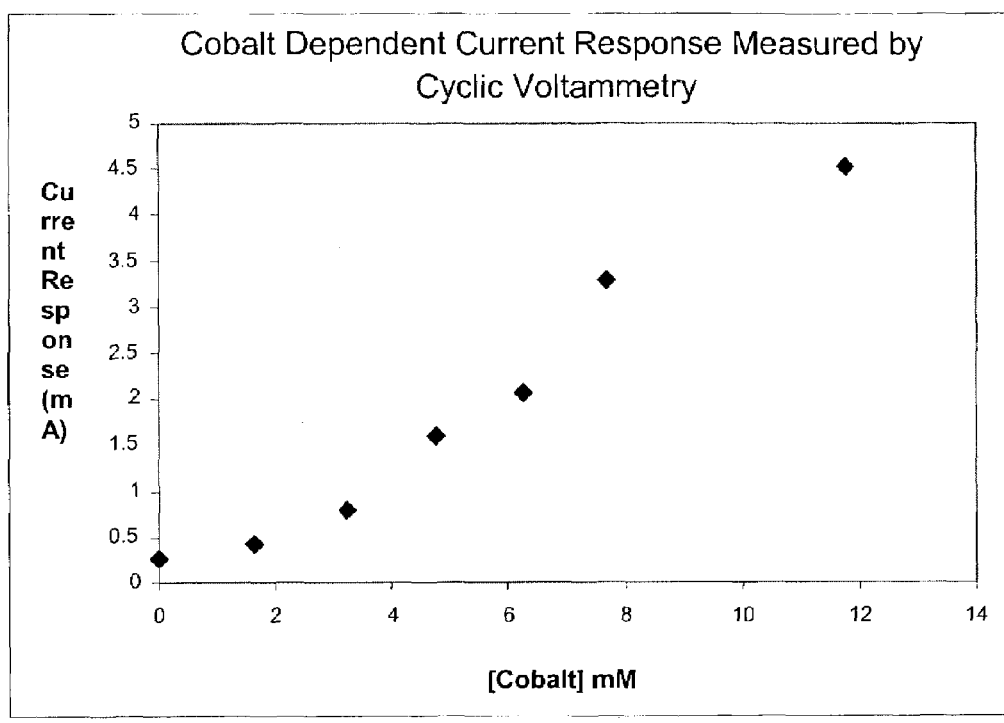
FIG. 6 shows a cobalt dependent current response measured by cyclic voltammetry.

Direct measurement of cobalt in a biological sample can be made using amperometric or scanning voltammetric techniques as described in Examples 3 and 4 and as illustrated in FIGS. 5 and 6. Such methods can be used to generate standard curves useful in diagnosis of clinical samples.

The specificity of cobalt binding to albumin has been described for the ACB Test (Journal of Clinical Ligand Assay on Cardiac Markers. Accepted for Publication summer 2002), and is further supported by electrochemical studies as described in the Examples. As described therein, for a constant concentration of Co ion in a sample, the cobalt current peak is inversely dependent on the concentration of albumin present in the sample.

Modifications to albumin are believed to occur as a result of exposure to ischemic tissue (PCT/US99/22905, filed Oct. 1, 1999). One such proposed modification is copper bound to the metal sequestering sites on albumin of which the N-terminus is the primary site. As described in the Examples, samples containing albumin that has been complexed with increasing concentrations of copper demonstrate increasing current due to the available cobalt ion.

As further described in the Examples, it has been observed that there is a strong correlation between diagnosis of an ischemic event via the subject electrochemical methods and diagnosis via the established ACB Test method.

Potential Differences Methods

Potential differences can be measured when there is a change in species activity relative to two "compartments." Ion selective electrodes are commonly used to measure these types of potential differences. Ion selective electrodes selectively measure activity of a species on the inner compartment of the electrode (on one side of the membrane) relative to the outer compartment (the outside of the membrane, or the bulk solution). The differences in activity on either side of the membrane lead to an electric potential difference across the membrane. Ion(s), for which the membrane is selective, diffuse across the membrane based on their concentration gradient. The side of the membrane with low activity will eventually build up charge in common (+/−) with the migrating ion preventing further ion migration at which time a constant potential between the two compartments is reached.

The potential difference between the two compartments, derived from the free energy equation, is as follows:

$$E=(RT/nF)\ln(A_1/A_2) \text{ or at } 25°\text{ C., } E=(0.05916/n)\log(A_1/A_2)$$

E=the resulting potential difference
R=constant (8.315 J/(mol·K))
T=Temperature in K
n=charge on the ion
$A_1$=the activity of the ion in one compartment
$A_2$=the activity of the ion in the second compartment
Activity is often used to estimate ion concentrations.

There are four basic types of ion selective electrodes: glass membrane electrodes, solid-state electrodes, liquid-based electrodes, and compound electrodes.

Glass membrane electrodes are typically used for monovalent cations. The most common example is a pH meter that is selective for H+, although different glass compositions are selective for different monovalent cations.

Solid-state electrodes use an inorganic salt as the membrane in which the ion of interest can be captured in a pocket in the crystal lattice. The ions can then migrate through the crystal lattice by moving from one adjacent pocket to the next. A common example is the fluoride electrode.

Liquid-based electrodes use a hydrophobic polymer membrane saturated with a hydrophobic liquid ion exchanger. In this case, the hydrophobic polymer membrane may have an ion "transporter" dissolved into it. An example would be apo-cyanocobolamine dissolved into an organic solvent which would be a selective ion exchanger for cobalt in a hydrophobic membrane.

Ion selective electrodes can be scaled down to microelectrodes with tip diameters as small as 10 µm allowing for very small volume measurements. Ion selective electrodes respond only to the uncomplexed ion, and can be "fine tuned" for selectivity relative to other (potentially interfering) ions by changing parameters discussed above. If the ionic strength of the solution remains constant during a measurement then the activity coefficient remains constant as well, and the measured activity of the ion is equivalent to the concentration of the ion.

The Apparatus

Figure 10:
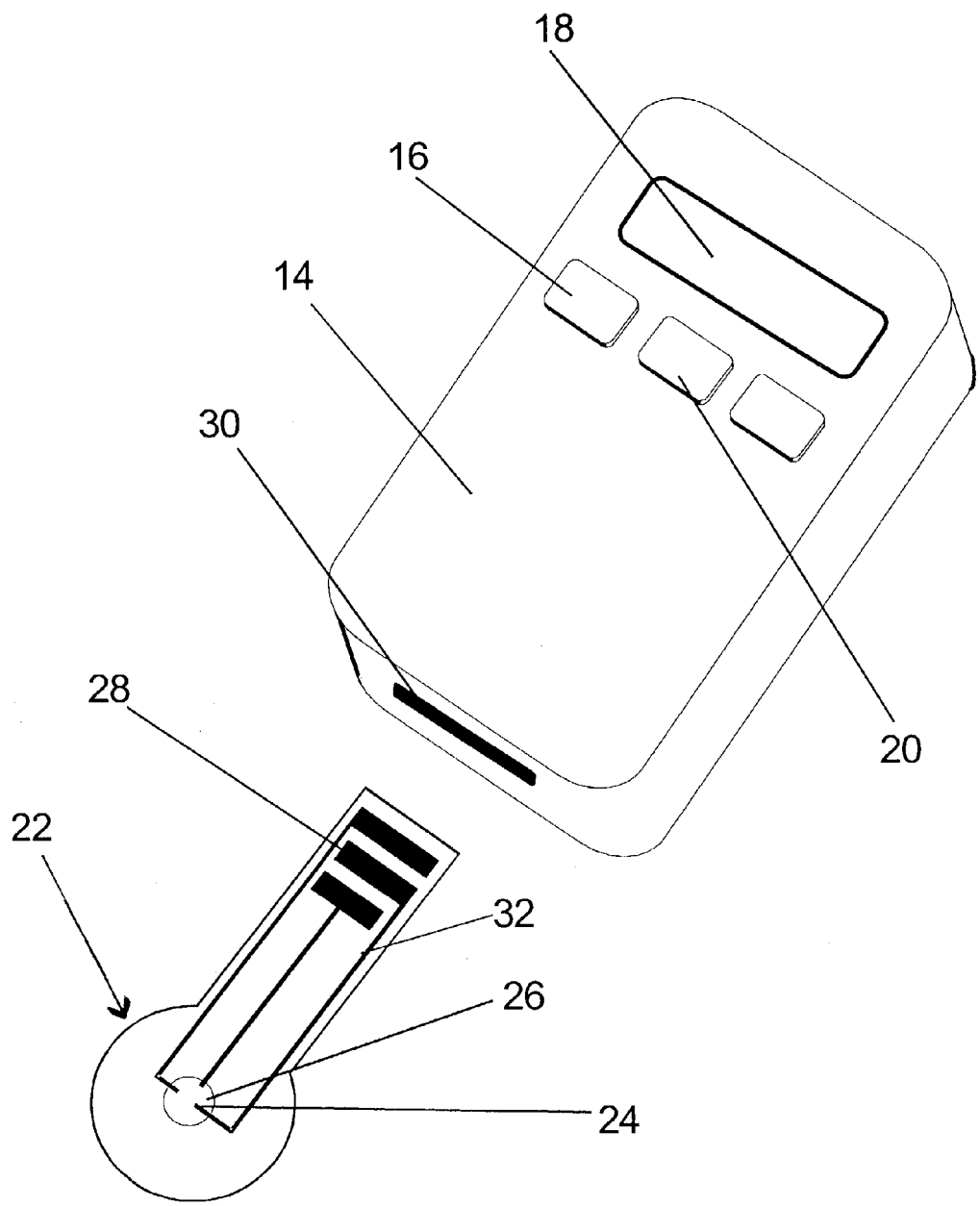
FIG. 10 illustrates a hand held, point of care device suitable for practicing the methods of the subject invention.

The device illustrated herein in FIG. 10 can be used in either the current or the potential difference embodiments of the invention. The device consists of an electronics module of suitable size to be held in the hand. It is housed in a rugged water resistant plastic material suitable for hospital use where it may be in contact with body fluids such as blood, and therefore must be easily cleanable. The housing 14 contains the read electronics, power source (e.g., battery), and other components required to perform the measurement operations.

On the housing are one or more function keys 16 and 20 that can be used by the operator for initiating the measurement operation, altering parameters, and entering data such as patient ID. For clarity, FIG. 10 shows three function keys, but there could be any number from zero to a full keyboard to allow text input.

A feature that may also be available on the housing is a mechanism for communication with a laboratory information system (mechanism not shown). For example, this could be a direct electrical connection (e.g., RS232 serial, and 100BaseT Ethernet communications), an infrared link (transmission via infrared light pulses) or a wireless link (radio transmitter/receiver).

On the front of the housing in view of the operator is optionally a display 18 which is used for displaying results of the potential difference or current measurements, and other communications such as system status, fault conditions, battery low indicator and the like.

At one end of the housing is an aperture 30 into which the sample strip is inserted to allow the results to be read.

The sample strip is also illustrated in FIG. 10. The strip 22 may be disposable and preferably is made of an insulating and waterproof material. It contains a sample well or vessel 26. In the well are electrodes 24, as described above. Each electrode 24 is connected via its corresponding conductor or trace 32 (which could be a printed conductor or a wire), which is electrically continuous with its corresponding strip contact 28.

In use, a sample of body fluid (e.g., blood, urine, saliva) is introduced to the sample well. After a suitable time, the test device is introduced into the aperture 30 in the housing 14. (Note: to minimize operator handling of a "loaded" strip, and therefore contact with biohazard, it may be better to add the biological sample to a strip that has already been inserted into the aperture). Electrical contact is made between the strip contacts 28 and contacts in the module aperture (not shown) which are in electrical continuity with the electronics which are also connected to the optional display 18. Electrical measurements are made on the sample via the electrodes 24. After the display 18 indicates the results of the measurement sequence and/or the results of the test, the disposable test device may be removed from the module and discarded.

As is appreciated by those of skill in the art, alternatives to the device of FIG. 10 such as table top devices can be used to practice the subject invention. Additionally, the subject methods can be automated to reduce processing time and costs associated with analyses.

Applications

The methods described herein for the diagnosis of an ischemic event have many clinical applications. In one embodiment, the subject methods can be used to detect exercise-induced ischemia. Levels of ischemia in patients at rest and during exercise can be compared to assess patients with known or suspected ischemic conditions. Initially, a patient sample may be obtained and analyzed; then the patient undergoes a treadmill test or other exercise; another patient sample may then be obtained and analyzed; and the results of the tests are compared. These steps may be repeated at additional times (e.g., 3 months, 6 months or 1 year later) for further assessment. This application is useful in assessing the patency of an in-situ coronary stent or the efficacy of a percutaneous cardiac intervention (e.g., an angioplasty procedure).

The subject method can also be used to detect the existence of ischemia provoked by exercise in an otherwise asymptomatic patient (silent ischemia). Again, the a sample is taken from the patient, the patient is subject to a treadmill test or the like, and a second sample is obtained. Detection of ischemia in an otherwise asymptomatic patient can reduce the severity of coronary artery disease or other ischemic conditions. Silent ischemia may also be detected with a single sample, i.e., not in the context of an exercise-induction test.

In another embodiment, the subject methods can be used as a method for ruling out the existence of ischemia in a patient, particularly in patients that possess one or more cardiac risk factors. Such risk factors include: age greater than 50, history of smoking, diabetes mellitus, obesity, high blood pressure, high cholesterol, and strong family history of cardiac disease. Ruling out an ischemic event is important in proper allocation of medical resources: patients who are known to not be experiencing an ischemic event need not receive the full gamut of tests and treatment reserved for those patients who are in fact experiencing acute coronary syndrome. In one embodiment of this application, an initial sample is obtained from the patient, who is then subjected to an exercise treadmill test or other exercise, followed by the taking of a second sample. Comparison of the test results will reveal whether the ischemic event is induced only under the elevated metabolic conditions of exercise. Additionally, ruling out an ischemic event may also be done with a single patient sample, i.e., not in the context of the exercise-induction test.

The subject methods can be used to evaluate a patient presenting with angina or angina-like symptoms to detect the occurrence of a myocardial infarction. The results of the subject methods and the results of an ECG are compared for consistency in indicating ischemia and myocardial infarction.

Additionally, the subject methods can be used in the assessment of the efficacy of a percutaneous cardiac intervention such as an angioplasty procedure. Patient samples are taken before and at predetermined times after the procedure to assess the patient's ischemic status.

The subject methods can be used to supplement ECG results so as to determine the occurrence or non-occurrence of an ischemic event. This application may find particular use in patients undergoing surgery.

The subject methods can also be used to detect the occurrence of a temporally-limited ischemic event in a patient Temporally-limited ischemia includes ischemic events associated with, e.g., exercise or drug use.

The subject method can also be used to detect an ischemic event in a patient suffering from stroke-like signs. Use of the subject methods in this situation permits the distinction between an ischemic stroke and a hemorrhagic stroke.

Additionally, the subject methods can be used to assess the efficacy of thrombolytic or other drug therapy such as drugs to attenuate an ischemic event by conditioning ischemic myocardium. Patient samples are obtained before and at predetermined times after the drug therapy to detect any reduction in ischemic events due to the therapy.

Further, the subject methods can be used for the detection of placental insufficiency in a pregnant woman. The sample is typically taken from the mother; the presence of IMA can be indicative of an ischemic condition in the placenta

EXAMPLES

Example 1

Correlation of Cobalt Concentration with Measured Current

Adsorption or stripping voltammetry was used to correlate increasing cobalt concentration in a sample with generated current. Cobalt was added to a biological fluid and allowed time to bind to non-modified albumin. The kinetics of cobalt binding to albumin were tested previously and showed the binding reaction was faster than 1 minute. A series of potentials were applied, in this case in the form of a cyclic voltammogram, although potentials may also be applied step-wise, resulting in a redox reaction of the available cobalt, thus causing cobalt to adsorb to the working electrode. A second cobalt redox reaction measured the amount of cobalt absorbed to the electrode in the form of current as a range of potentials is scanned. Cobalt dependent current peaks generated in this fashion are shown over a concentration range of 56–174 mM cobalt in FIG. 3. A change in current consistent with a change in cobalt concentration was observed demonstrating that the current being generated is in fact cobalt dependent.

Example 2

Use of Complexing Agents to Enhance Current Associated with Non-Sequestered Metal Ion The complexing agent DMG was added to samples to enhance the signal response of cobalt ion. Increasing concentrations of cobalt were added to a biological sample and allowed to bind to non-modified albumin. A constant concentration of DMG was then added in excess of the cobalt concentration to the sample and voltammetry techniques were used to detect the Co(DMG)$_2$ complex in the form of current. In this case, a cobalt concentration range of 0.094–1.780 mM was used and showed the appropriate change in current value relative the change in cobalt concentration. In control experiments, cobalt and DMG were added separately and showed no current response at the appropriate potentials, indicating that the signal generated is dependent on the formation of Co(DMG)$_2$ complex and is therefore proportional to the amount of available cobalt present in the system.

Further work was done using the complexing technique to demonstrate the clinical utility in determining the population difference between ischemic and non-ischemic individuals. Ischemia positive samples were determined using the ACB™ Test (Ischemia Technologies, Inc., Denver, Colo.) using the 95$^{th}$ percentile of the upper limit of normal as the defined cutoff (National Committee for Clinical Laboratory Standards, *How to Define and Determine the Reference Intervals in the Clinical Laboratory; Approved Guideline*, NCCLS 1995; Document C28-A Vol.15 No.4). Any value higher than this is regarded as "ischemic", and any value lower than this is regarded as "non-ischemic". A two-tailed t-test showed that electrochemical techniques using a cobalt complexing agent showed a significant separation between ischemic and non-ischemic samples (p-value=0.01).

Example 3

Measurement of Cobalt Ion Using Amperometry

Available cobalt added to a biological sample can be directly measured using an amperometric technique. In these experiments, cobalt was added to the sample sequentially over time, while a potential appropriate to drive a redox reaction was applied to the system. As is shown in FIG. 5, the change in cobalt concentration in the sample was detected as changes in output current, demonstrating a saturating relationship with cobalt at high concentrations.

Example 4

Measurement of Cobalt Ion Using Scanning Voltammetry

Available cobalt may also be measured directly in a biological sample using cyclic voltammetry or similar scanning potential techniques such as step voltammetry. Cobalt, excess to the amount of albumin present in the sample, was added and allowed to bind to non-modified albumin. The appropriate potential range was then scanned such that a cobalt dependent current was measured. FIG. 6 shows the resulting plot of increasing cobalt current response over an increasing range of cobalt concentrations (0–1200 µM), indicating that the current response is cobalt dependent and that a relative concentration range can easily be detected.

Example 5

Specificity of Cobalt Binding to Albumin as Measured by Current

Figure 7:
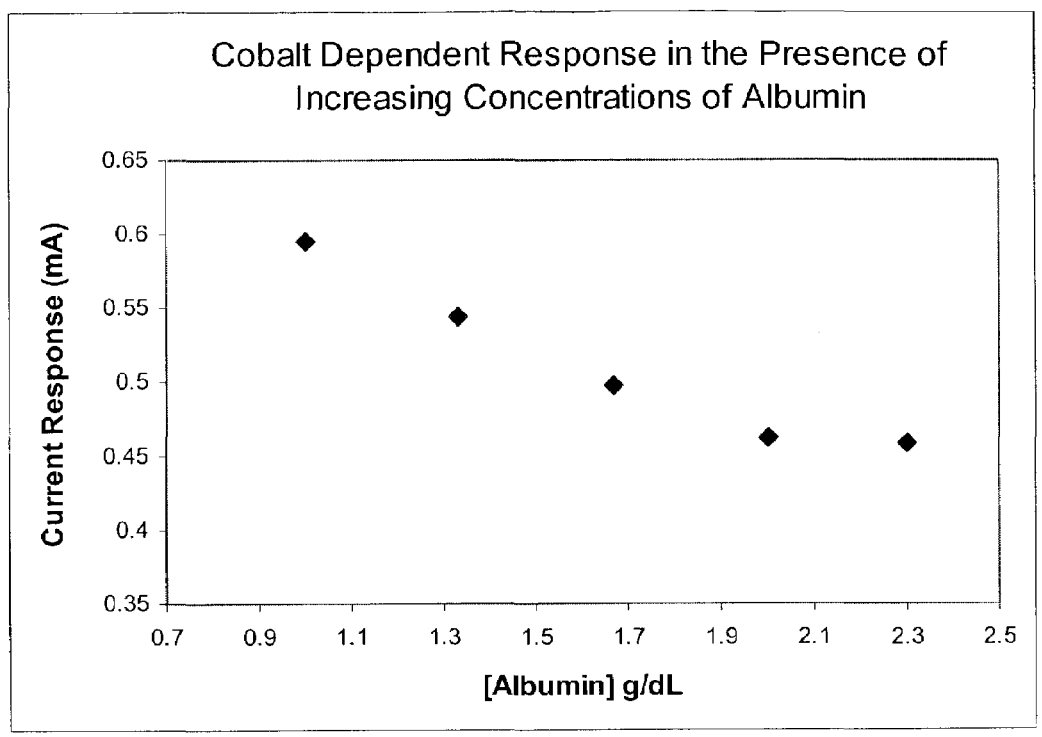
FIG. 7 shows a cobalt dependent response in the presence of increasing concentrations of albumin.

The specificity of cobalt binding to albumin is supported by an illustration of the dependence of the cobalt current peak on the concentration of albumin present in the sample. Biological samples were spiked with increasing concentrations of albumin. A constant concentration of cobalt was then added to each sample and allowed to bind to non-modified albumin. The appropriate potential range to produce a cobalt current peak was then scanned. FIG. 7 shows the expected decrease in the cobalt current response with increasing concentrations of albumin, which is indicative that albumin sequesters cobalt from detection by electrochemical methods.

Example 6

Increased Current and Cobalt Ion with Increased Copper

Figure 8:
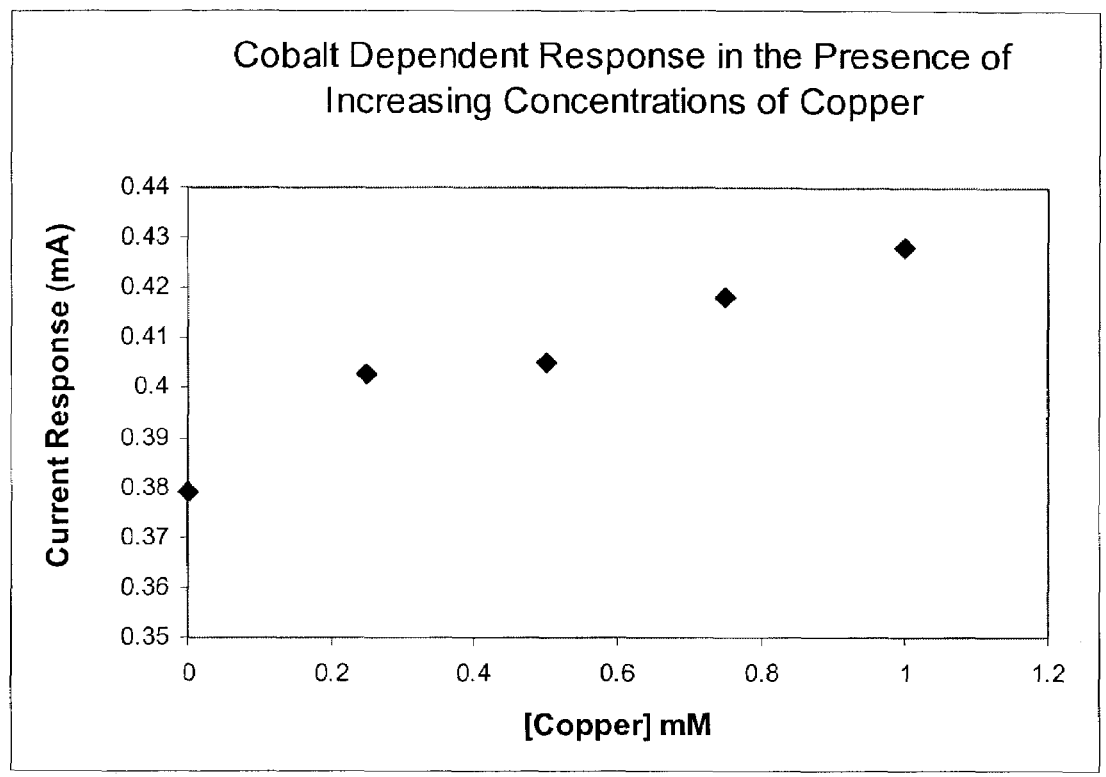
FIG. 8 shows a cobalt dependent response in the presence of increasing concentrations of copper.

One of the proposed ischemia mechanisms involves the binding of copper to the N-terminus of albumin during an ischemic event. Ischemic samples were simulated by adding increasing concentrations of copper to a normal sample, a method that has shown an average increase in ACB value of 60% at 1 mM copper. Cobalt was then added to the sample and the appropriate potential range was scanned to produce a cobalt dependent current peak resulting from the redox reaction of cobalt. FIG. 8 shows the response in the electrochemical system under these conditions. As copper concentrations increase and the copper becomes bound to the sequestering sites on albumin, there are fewer sites available to sequester cobalt and therefore there is an increase in the cobalt current response. At 1 mM copper, the increase in electrochemical output signal (current) is approximately 30%. The increased current is due to cobalt because there will be no competition in binding to the primary site as copper has a higher affinity for albumin than does cobalt ($10^6$ and $10^4$ respectively). In addition, the redox potential for copper does not overlap with the redox potential of cobalt.

Example 7

Figure 9:
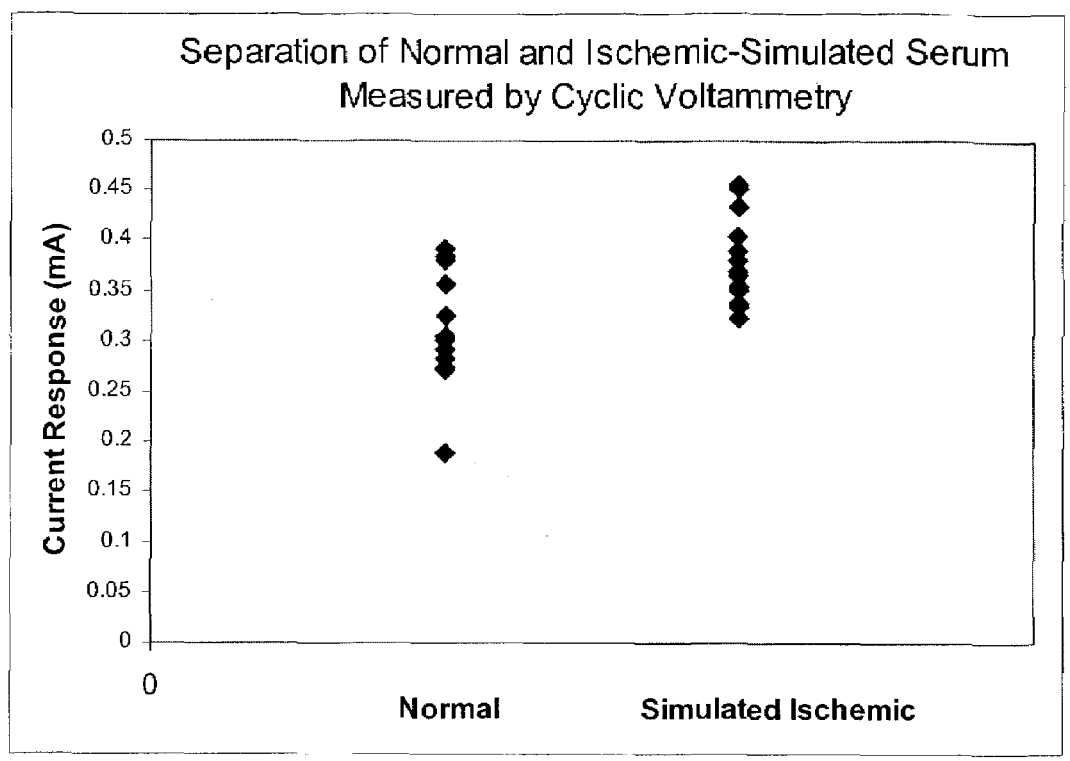
FIG. 9 shows a significant population difference between normal and modified albumin present in a biological fluid as measured by cyclic voltammetry.

Correlation of Diagnosis via Current Detection Method and Diagnosis via ACB Test Method Normal samples loaded with copper give an increased ACB value resulting in a shift from the normal to the ischemic range. Copper loaded samples determined by the ACB Test to be in the ischemic range and samples determined by the ACB Test to be non-ischemic were used to create two populations of samples. These samples were tested by the addition a constant concentration of cobalt and scanning the appropriate potentials to produce a cobalt current peak. The resulting current response from these populations was used to determine if the populations could be statistically separated by this method. A two-tailed t-test was used and showed a significant population difference (p-value=0.0040) as shown in FIG. 9.

Example 8

Potential Difference Method for Detection of Ischemia

Ion selective electrodes (ISE) are commonly used in the clinical setting to measure electrolytes (e.g., Na+ and K+) in biological samples. Valinomycin is often used to make a membrane selective for potassium (Cattrall, R. wt al. (1974) Anal. Chem. 46(14):2223–6). ISE have also been shown to be useful in measuring copper binding to serum albumins (Mohanakrishnan, P. et al. (1982) J. Pharm. Sci. 71(10): 1180–2), thus demonstrating the ability of ISE to measure free metal ions in a complex sample matrix. Altura et al. (1996) Scand. J. Clin. Lab. Invest. Suppl. 224:211–34, demonstrated that there was no observable difference between ISE signals obtained from plasma and serum samples when measuring magnesium concentrations.

As discussed herein and in PCT/US99/22905, an existing method for detecting albumin-cobalt binding (ACB) involves the detection of free cobalt in a patient sample using a calorimetric reaction. The subject example demonstrates how free cobalt can be detected in biological samples using an ion selective electrode and then correlating the results to the current ACB Test format.

Ion Selective Electrode Design

1. A cobalt selective membrane is made by making a saturated solution of apo-cobolamine in a non-aqueous solvent such as 3-nitro-o-oxylene. The solvent is placed in a glass tube and apo-cobolamine is added such that the total concentration of apo-cobolamine is too high to totally dissolve into the non-aqueous solvent. This mixture serves as the cobalt selective membrane.
2. A glass capillary tube either with or without a filament and a pre-pulled inner diameter of 1.0–1.5 mm serves as the electrode body.
3. The inside of the glass capillary tube is cleaned by running acetone through it. This wash will remove any petroleum products introduced during manufacturing.
4. The acetone residue is rinsed away by running de-ionized water through the tube and baking in an oven for 30 minutes to dry.
5. The capillary tube is pulled in an electrode puller and the tip opening is adjusted such that the outer tip diameter is 10–70 um. The tip opening can be adjusted by either "bumping" the tip with a glass rod, or the tip can be snipped using a razor blade or dissection scissors.
6. The electrode can then be silanized by placing 1 drop of chlorodimethylsilane in the tip of the electrode using a micro Hamilton syringe.
7. The electrode is then placed in an oven at 180° C. for 1 hour with the tip upright such that the evaporative fumes from the chlorodimethylsilane will pass through the small tip.
8. The tip can then be filled with the cobalt selective membrane using the micro Hamilton syringe. Caution must be used not to introduce bubbles in the electrode tip.
9. The micro Hamilton syringe can then be used to backfill the electrode with 25 mM cobalt chloride solution using caution not to "mix" the cobalt selective membrane and the cobalt chloride solution. The cobalt chloride solution should be layered directly on top of and in contact with the membrane, but the two layers should not mix.
10. A silver wire is then placed through the large end of the electrode into the cobalt chloride solution. The wire will function as the working electrode contact. The top of the electrode may be sealed to keep the wire in place. Care must be used to ensure that the wire does not come in contact with the cobalt selective membrane.
11. A silver/silver chloride wire is used as the reference electrode. (A silver/silver chloride reference electrode with a salt bridge may be used to improve the signal.) The working electrode wire and the reference electrode wire are connected to an electrostat for recording. An electrostat has a high input impedance which ensures that the potential difference between the working and reference electrodes is the only thing being measured. It may be possible to substitute the electrostat with a voltmeter with sufficient input impedance. Connectors with sufficient input impedance requirements may also be used with a standard voltmeter.

Generating a Standard Curve

A standard curve is generated such that the resulting potential difference between the working and reference electrodes can be translated into free cobalt concentrations. A sample consisting of 6 g/dL IgG in 0.9% NaCl is used to simulate the expected sample matrix conditions in which there is no capacity to sequester added cobalt. The working electrode and the reference electrode are both placed in contact with the sample. Varying concentrations (5, 10, 15, 20 and 25 mM) of cobalt chloride solutions are added to the sample and the resulting potentials are recorded. The plotted results of potential versus cobalt concentration should ideally be linear or a non linear function can be used to fit the curve. The line or curve fitting equation for the plot is recorded such that subsequent experimental measurements of free cobalt can be quantified.

Equipment and reagents should be recalibrated before sample testing if the working electrode has not been used for 24 hours or if there is a reagent change.

Testing the Selectivity of the ISE for Cobalt

The selectivity of the ion selective electrode is determined by the selectivity coefficient.

$K_{X,Y}$=Response to Y/Response to X, where in this case $X=Co^{2+}$ and

Y=any other species of size, charge or properties similar to cobalt that the ISE may respond to.

Y may also include free metal ions of high concentration found in the sample type to be tested. Ideally, the selectivity coefficient should be very small (K<<1) indicating that the electrode is highly selective for cobalt.

Three potentially interfering metals in biological samples are $Fe^{2+}$, $Ni^{2+}$ and $Cu^{2+}$. Although it is unlikely that these metals will be found free in a sample, the selectivity for cobalt using the ion selective electrode should be tested and shown to be adequate.

Individual standard curves are generated using $Fe^{2+}$, $Ni^{2+}$ and $Cu^{2+}$ as the analytes.

A sample consisting of 6 g/dL IgG in 0.9% NaCl is used to mimic the physiological matrix. Varying concentrations (5, 10, 15, 20, and 25 mM) of $FeCl_2$ are added to the sample and the resulting potentials between the working electrode and the reference electrode at each concentration are recorded. The selectivity coefficient for $Co^{2+}$ over $Fe^{2+}$ is calculated by taking the potential response from 5 mM $Fe^{2+}$ and dividing by the potential response from 5 mM $Co^{2+}$. This calculation is continued for all concentrations of $Fe^{2+}$ tested. All selectivity coefficients should be very small.

This process is repeated for the same concentrations for $Ni^{2+}$ and $Cu^{2+}$.

Testing Patient Samples

The working and reference electrodes are placed in the biological sample (e.g., plasma, serum, whole blood). No potential difference or very little potential difference should be measured at this time as the working electrode can only measure free cobalt of which there should very little or none present in the sample. If a signal is measured it is assumed to be background noise and can be subtracted from the final measurement. 25 mM cobalt chloride solution is added to the sample and the stabilized potential difference between the working electrode and reference electrode is measured. When the signal has stabilized, all the albumin sites capable of binding and sequestering cobalt are occupied and the signal (in millivolts, mV) is produced from available non sequestered cobalt in the sample.

Available non sequestered cobalt in the sample can then be quantified using the stabilized potential measurement and referenced to the appropriate calibration curve.

Correlation of ISE and ACB

The existing albumin-cobalt binding (ACB) Test set forth in PCT/US99/22905 measures IMA in samples by calorimetrically measuring available non-sequestered cobalt. A correlation between the ACB method and the ISE method can be established by testing samples using both methods. A plot is made where mV results from the ISE method are plotted on the y-axis and the ACB (U/mL) results are plotted on the x-axis. The correlation coefficient for the resultant line is an indication of the relative performance of the ISE method relative to the ACB Test.

A bias plot should be generated by calculating the percent difference between the corresponding individual samples as measured by both methods to determine the accuracy of the new method.

Using clinical data established for the ACB test, available non-sequestered cobalt concentration as measured by the potential difference protocol described herein can be compared to predetermined cobalt values that have been found to be diagnostic of an ischemic event.

The invention claimed is:

1. A method for in vitro detection or measurement of albumin derivatives, which can be diagnostic of an ischemic event, said method comprising:
   a) providing a patient sample comprising albumin and/or derivatives thereof in a vessel that is connected to an electrochemistry apparatus;
   b) operating the electrochemistry apparatus to utilize an electrochemical technique;
   c) optionally measuring a background characteristic electrochemical output signal of the sample;
   d) adding a known amount of a transition metal ion to the sample, whereby at least some of the ion binds to albumin metal sequestering sites and remaining ion is non-sequestered;
   e) optionally adding an indicator or amplifier to the sample to bind to the non-sequestered ion;
   f) measuring a characteristic electrochemical output signal associated with the non-sequestered ion;
   g) optionally using a standard curve to convert the measured output signal of step (f) to a converted value;
   whereby the measured electrochemical output signal or the converted value, if it exceeds a predetermined value, can be diagnostic of an ischemic event.

2. The method of claim 1, wherein the known amount of metal ion is an excess amount.

3. The method of claim 1, wherein the characteristic electrochemical output signal is selected from the group consisting of current and voltage.

4. A method for in vitro detection or measurement of albumin derivatives, which can be diagnostic for an ischemic event, said method comprising:
   a) providing a patient sample comprising albumin and/or derivatives thereof in a vessel having a reference electrode and a working electrode, said electrodes being operably connected to a potentiostat;
   b) operating the potentiostat to apply a potential to the sample;
   c) optionally offsetting a background current from redox reactions in the sample to zero;
   d) adding a known amount of a transition metal ion to the sample, whereby at least some of the ion binds to albumin metal sequestering sites and remaining ion is non-sequestered by albumin;
   e) optionally providing an indicator or amplifier to the sample to bind to the non-sequestered metal ion;
   f) permitting the reaction of ion and albumin to reach equilibrium or a predetermined processing time; and
   g) measuring the current associated with the non-sequestered ion;
   h) optionally using a standard curve to convert the measured current to a converted value;
   whereby the measured current or converted value, if it exceeds a predetermined value, can be diagnostic of an ischemic event.

5. The method of claim 4, wherein the known amount of metal ion is an excess amount.

6. The method of claim 4 wherein said vessel further comprises an auxiliary electrode in said vessel that is operably connected to said potentiostat.

7. The method of claim 6, wherein the known amount of metal ion is an excess amount.

8. The method of claim 4 wherein said working electrode further comprises an indicator or amplifier to bind to non-sequestered metal ion.

9. The method of claim 4, wherein said diagnosed ischemic event is cardiac ischemia.

10. The method of claim 4, wherein said diagnosed ischemic event is silent ischemia.

11. The method of claim 4, wherein the diagnosed ischemic event is angina.

12. The method of claim 4, wherein the diagnosed ischemic event is myocardial infarction.

13. The method of claim 4, wherein the diagnosed ischemic event is temporally-limited isehemia.

14. The method of claim 4, wherein the diagnosed ischemic event is bowel ischemia.

15. The method of claim 4, wherein the diagnosed ischemic event is brain ischemia.

16. The method of claim 4, wherein the diagnosed ischemic event is placental insufficiency.

17. The method of claim 4, wherein said diagnosis of the ischemic event is used to evaluate efficacy of an in-situ coronary stent.

18. The method of claim 4, wherein said diagnosis of the ischemic event is used to evaluate efficacy of percutaneous cardiac intervention.

19. The method of claim 4, wherein said diagnosis of the ischemic event is used to evaluate efficacy of drug therapy.

20. A method of detecting or measuring exercise-induced ischemia by determining the level of ischemia in a patient during exercise, and before exercise, after exercise or both, and comparing said levels, wherein ischemic events are detected or measured using the method of claim 4.

21. A method for in vitro detection or measurement of albumin derivatives which may be diagnostic for an ischemic event, said method comprising:
   a) providing a patient sample comprising albumin and/or derivatives thereof in a vessel having an ion selective electrode and a reference electrode, said electrodes being operably linked to an electrostat or a voltmeter, said ion selective electrode comprising a barrier that is selectively permeable to a transition metal ion;
   b) operating the electrostat or voltmeter to measure the potential difference between the reference electrode and the ion selective electrode in contact with the sample;
   c) optionally offsetting a background potential difference of the sample;
   d) adding a known amount of said transition metal ion to the sample, whereby at least some of the ion binds to albumin metal sequestering sites and remaining ion is non-sequestered;
   e) optionally providing an indicator or amplifier to the sample to bind with the non-sequestered metal ion;

f) permitting the non-sequestered metal ion to cross the membrane of the ion selective electrode; and g) measuring a voltage associated with an ion activity difference across the ion selective electrode's barrier;

h) optionally using a standard curve to convert the measured voltage of step (g) to a converted value;

whereby the measured voltage or the converted value, if it exceeds a predetermined value, can be diagnostic of an ischemic event.

22. The method of claim 21, wherein the diagnosed ischemic event is cardiac ischemia.

23. The method of claim 21, wherein said diagnosed ischemic event is silent ischemia.

24. The method of claim 21, wherein the diagnosed ischemic event is angina.

25. The method of claim 21, wherein the diagnosed ischemic event is myocardial infarction.

26. The method of claim 21, wherein the diagnosed ischemic event is temporally-limited ischemia.

27. The method of claim 21, wherein the diagnosed ischemic event is bowel isohemia.

28. The method of claim 21, wherein the diagnosed ischemic event is brain isehemia.

29. The method of claim 21, wherein the diagnosed ischemic event is placental insufficiency.

30. The method of claim 21, wherein said diagnosis of the ischemic event is used to evaluate the efficacy of an in-situ coronary stent.

31. The method of claim 21, wherein said diagnosis of the ischemic event is used to evaluate the efficacy of a percutaneous cardiac intervention.

32. The method of claim 21, wherein said diagnosis of the ischemic event is used to evaluate the efficacy of drug therapy.

33. A method of detecting or measuring exercise-induced ischemia by determining the level of ischemia in a patient during exercise, and before exercise, after exercise or both, and comparing said levels, wherein ischemic events are detected or measured using the method of claim 21.

* * * * *